US010278565B2

(12) United States Patent
Wieters

(10) Patent No.: US 10,278,565 B2
(45) Date of Patent: May 7, 2019

(54) ENDOSCOPE HAVING A DISTAL ELECTRICAL FEED-THROUGH, AND METHOD FOR ASSEMBLING AN ENDOSCOPE

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 323 days.

(21) Appl. No.: 15/263,601

(22) Filed: Sep. 13, 2016

(65) Prior Publication Data
US 2016/0374543 A1 Dec. 29, 2016

Related U.S. Application Data

(63) Continuation of application No. PCT/EP2015/055258, filed on Mar. 13, 2015.

(30) Foreign Application Priority Data

Mar. 14, 2014 (DE) .................. 10 2014 204 784

(51) Int. Cl.
*A61B 1/00* (2006.01)
(52) U.S. Cl.
CPC ........ *A61B 1/00188* (2013.01); *A61B 1/0011* (2013.01); *A61B 1/00071* (2013.01);
(Continued)
(58) Field of Classification Search
CPC ... A61B 1/00188; A61B 1/05; A61B 1/00096; A61B 1/0011; A61B 1/00114;
(Continued)

(56) References Cited

U.S. PATENT DOCUMENTS 3,794,039 A * 2/1974 Kollner .............. A61B 18/0218
606/22
4,759,346 A * 7/1988 Nakajima ................ A61B 1/05
348/65
(Continued)

FOREIGN PATENT DOCUMENTS

CN    87207404 U    10/1988
CN    101061943 A    10/2007
(Continued)

OTHER PUBLICATIONS

Japanese Office Action dated Jun. 12, 2018 in Japanese Patent Application No. 2016-557310.
(Continued)

*Primary Examiner* — John P Leubecker
(74) *Attorney, Agent, or Firm* — Scully, Scott, Murphy & Presser, P.C.

(57) ABSTRACT

An endoscope having a distal electrical feed-through, the endoscope including: an endoscope shaft having a distal objective unit comprising an electromagnetic actuator and a distal optical assembly that can be shifted in a longitudinal direction by actuation of the actuator, the endoscope shaft having a proximal unit having a proximal optical assembly arranged after the distal optical assembly in the direction of incident light, the objective unit is rotatable relative to the proximal unit about a longitudinal axis during assembly of the endoscope and is fixed rotationally relative to the proximal unit after assembly; and a cable for supplying current to the actuator, the cable being fed from the proximal unit to the objective unit, the cable having an excess length at a transition from the proximal unit to the objective unit, such excess length being at least half of the outer circumference of the objective unit.

7 Claims, 1 Drawing Sheet

(52) U.S. Cl.
CPC ...... *A61B 1/00096* (2013.01); *A61B 1/00114* (2013.01); *A61B 1/0008* (2013.01)

(58) Field of Classification Search
CPC ... A61B 1/0008; A61B 1/051; A61B 1/00071; H04N 5/2254; H04N 2005/2255
See application file for complete search history.

(56) References Cited

U.S. PATENT DOCUMENTS

| | | | | |
|---|---|---|---|---|
| 4,928,699 | A * | 5/1990 | Sasai | A61B 1/00071 600/110 |
| 5,176,141 | A * | 1/1993 | Bom | A61B 8/12 600/467 |
| 7,074,181 | B2 * | 7/2006 | Futatsugi | A61B 1/05 600/110 |
| 8,777,937 | B2 * | 7/2014 | Kroeckel | A61B 5/055 606/33 |
| 9,385,580 | B2 | 7/2016 | Wieters et al. | |
| 2003/0050534 | A1 * | 3/2003 | Kazakevich | A61B 1/0607 600/178 |
| 2009/0303619 | A1 * | 12/2009 | Iwasaki | A61B 1/0008 359/811 |
| 2011/0201884 | A1 | 8/2011 | Kishioka | |
| 2013/0193778 | A1 * | 8/2013 | Wieters | A61B 1/00133 310/12.04 |
| 2013/0314517 | A1 * | 11/2013 | Makiyama | A61B 1/045 348/65 |
| 2016/0213239 | A1 * | 7/2016 | Fujii | G02B 23/2438 |
| 2017/0065157 | A1 * | 3/2017 | Iwasaki | A61B 1/00 |
| 2017/0319047 | A1 * | 11/2017 | Poulsen | A61B 1/0008 |

FOREIGN PATENT DOCUMENTS

| | | |
|---|---|---|
| CN | 103026429 A | 4/2013 |
| DE | 102011006814 A1 | 1/2012 |
| JP | S49-045307 Y | 12/1974 |
| JP | H02-018513 A | 1/1990 |
| JP | H02-183214 A | 7/1990 |
| JP | H09-005602 A | 1/1997 |
| JP | H09-080513 A | 3/1997 |
| JP | 2007-244604 A | 9/2007 |
| JP | 2013-530672 A | 7/2013 |
| JP | 5385483 B1 | 10/2013 |
| WO | WO 2013/080608 A1 | 6/2013 |

OTHER PUBLICATIONS

Chinese Office Action dated Jun. 28, 2017 in Chinese Patent Application No. 201580013462.X.
International Search Report dated May 11, 2015 issued in PCT/EP2015/055258.

* cited by examiner

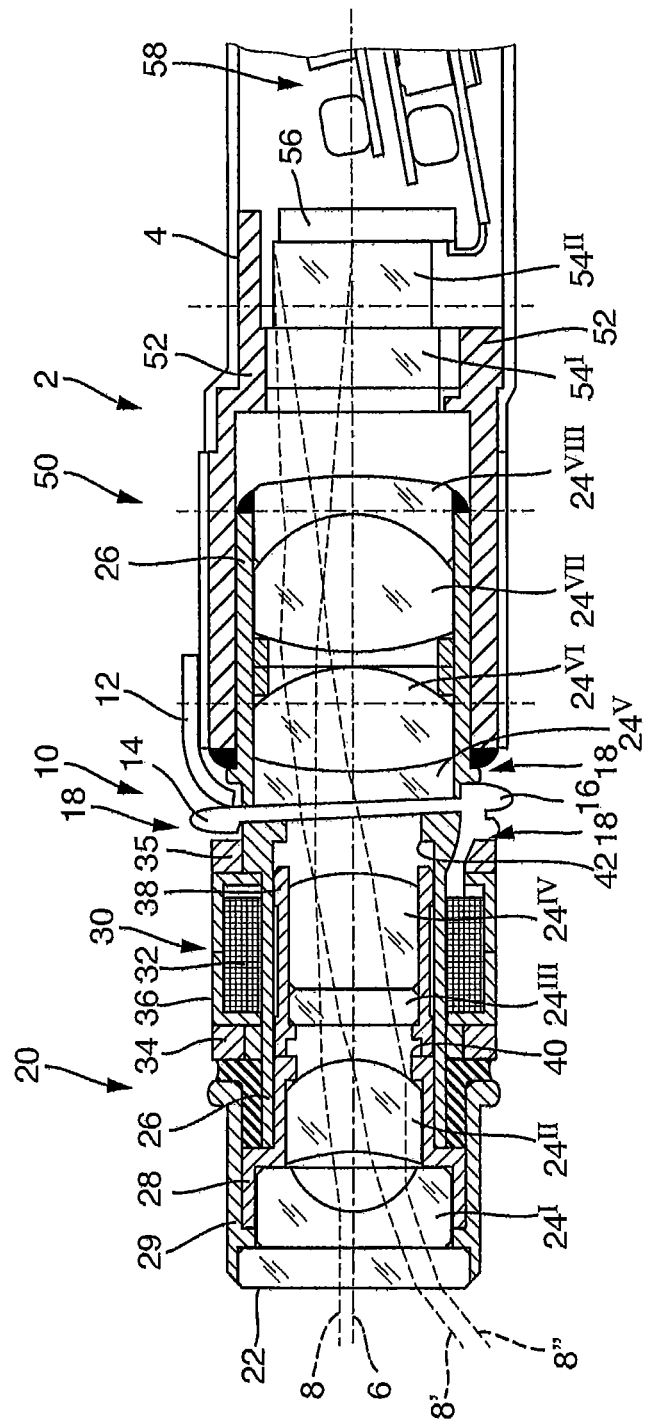

ENDOSCOPE HAVING A DISTAL ELECTRICAL FEED-THROUGH, AND METHOD FOR ASSEMBLING AN ENDOSCOPE

CROSS-REFERENCE TO RELATED APPLICATION

The present application is a continuation of PCT/EP2015/055258 filed on Mar. 13, 2015, which is based upon and claims the benefit to DE 10 2014 204 784.6 filed on Mar. 14, 2014, the entire contents of each of which are incorporated herein by reference.

BACKGROUND

Field

The present application relates to an endoscope having a distal electrical feed-through, said endoscope comprising an endoscope shaft with a distally arranged objective unit which comprises an electromagnetic actuator and a distal optical assembly that can be shifted in a longitudinal direction of the endoscope shaft by means of the actuator, and having a proximal unit with a proximal optical assembly arranged after the distal optical assembly in the direction of incident light, wherein the objective unit can be rotated in relation to the proximal unit about a longitudinal axis of the endoscope shaft during assembly of the endoscope, and is fixed in a rotationally secure manner in relation to the proximal unit after the assembly, wherein at least one cable for supplying current to the actuator is fed from the proximal unit to the objective unit. The present application further relates to a method for assembling an endoscope having a distal electrical feed-through.

Prior Art

With lens systems of video endoscopes and other endoscopes, flaws in the lens system are compensated by rotating the objective about its axis during the assembly of the endoscope of the image sensor unit until the best image quality is achieved. Then the objective is installed, or respectively fixed relative to the image sensor unit in this rotational alignment. In this manner, optical image flaws arising from tilting the lenses of the lens systems and other optically-active elements of the endoscope are minimized. Further distal elements, i.e. elements at the tip of the endoscope shaft of the endoscope, are for example electromagnetic actuators that can shift part of the lens groups of the lens system of the endoscope in order to, for example, adjust the focus range.

Known electromagnetic actuators used in endoscopes possess a coil with a coil wire having an end and start at a fixed point. To operate the actuator with maximum efficiency and hence enable maximum miniaturization, the coil wire must be guided through a small opening in a pole shoe, or respectively through a magnet. This fixes the coil wire in its position.

The coil wire must be electrically connected to a proximally arranged control unit, such as to a part from the image sensor unit, or respectively CCD unit. When there is a direct connection, it is impossible to rotate the objective relative to the CCD unit without shearing off the coil wires. It is also important for the coil wires to be already connected to the CCD during the rotation process so that the actuator can be operated and the recorded image can hence be completely evaluated.

SUMMARY

An object is therefore to create an electrical feed-through for an objective unit of an endoscope by means of which it is possible to set the optimum image quality during assembly.

Such object can be achieved by an endoscope having a distal electrical feed-through comprising an endoscope shaft with a distally arranged objective unit which comprises an electromagnetic actuator and a distal optical assembly that can be shifted in a longitudinal direction of the endoscope shaft by means of the actuator, and having a proximal unit with a proximal optical assembly arranged after the distal optical assembly in the direction of incident light, wherein the objective unit can be rotated in relation to the proximal unit about a longitudinal axis of the endoscope shaft during assembly of the endoscope, and is fixed in a rotationally secure manner in relation to the proximal unit after the assembly, wherein at least one cable for supplying current to the actuator is fed from the proximal unit to the objective unit, and the cable can have an excess length at the transition from the proximal unit to the objective unit, which excess length is at least half of, such as being at least equal to, the outer circumference of the objective unit.

Such solution considers that the electrical feed-through is kept rotationally flexible by providing an excess length of the cable which allows the objective unit to rotate relative to the proximal unit during assembly of the endoscope while the electrical connection is already established. The optical alignment of the objective unit relative to the proximal unit is also useful for the assembly of the endoscope. This makes it possible to evaluate the optimum image quality while the objective unit is rotating relative to the proximal unit that may comprise the image sensor. The excess length of the cable, which is configured to be flexible, can compensate for the rotation of the objective unit relative to the proximal unit by its deformation during the rotation.

The objective unit and the proximal unit can be held in a common holder that allows rotation of one or both units relative to each other during assembly as well as fixation, such as by adhesion, or by mechanical affixing means such as screws or rings. Other suitable fixing means or methods can also be used.

To enable the objective unit to rotate at least 360° relative to the proximal unit, the excess length is at least half the outer circumference of the objective unit around which the excess length of the cable will be, or respectively is wound and unwound. This enables a rotation of ±180°, i.e., a total of 360°. For safety's sake, a small extra amount is useful. During the rotation, the cable correspondingly winds around the objective unit.

If the entire excess length of the cable is not needed, such as where the optimum image is achieved before the maximum possible deflection, the excess cable can be placed in a loop around the objective, or respectively the objective unit. This is also useful for a translatory alignment of the objective unit and proximal unit, and not just for a rotational alignment. The aligned combination of the objective unit and proximal unit can then be inserted into a jacket tube, or first inserted into the jacket tube and then aligned.

In order to safely stow the excess length of the cable and simultaneously ensure that it winds and unwinds properly, a peripheral groove can be arranged between the objective unit and proximal unit in which the excess length of the cable runs, wherein the groove has a cross-sectional area that is at least three times, such as being more than five times, the cross-sectional area of the cable, as well as a height that at least corresponds to the thickness of the cable. The groove therefore provides the cable with sufficient space both in terms of the height, or respectively depth, as well as the overall cross-sectional area to wind and unwind and possibly execute a 180° turn. The objective unit can rotate during the assembly of the endoscope by at least ±180°, such as by at least 360°, relative to the proximal unit.

To prevent the cable from being shorn off from excessive rotation, rotation limiting stops can be provided that limit a maximum rotation of the objective unit relative to the proximal unit to the excess length of the cable. These rotation limiting stops can be located both on the optical unit as well as on the proximal unit, and can also be located, on the optical unit and a surrounding tube in which the optical unit and proximal unit are introduced. These can be projections that constitute a form-fit limit.

The objective unit can be shifted relative to the proximal unit in the longitudinal direction of the endoscope shaft.

The proximal unit can have at least one image sensor and one control and readout electronics, wherein the actuator is connected to the control and readout electronics such as by means of the cable. The electromagnetic actuator is controlled in this case by the control and readout electronics of the proximal unit.

An object can also be achieved by a method for assembling an endoscope having a distal electrical feed-through comprising an endoscope shaft with a distally arranged objective unit which comprises an electromagnetic actuator and a distal optical assembly that can be shifted in a longitudinal direction of the endoscope shaft by means of the actuator, and having a proximal unit with a proximal optical assembly arranged after the distal optical assembly in the direction of incident light, wherein the objective unit can be rotated in relation to the proximal unit about a longitudinal axis of the endoscope shaft, wherein at least one cable for supplying current to the actuator is fed from the proximal unit to the objective unit, such as an above-described endoscope, having the following method steps:

a) the cable is installed at the transition from the proximal unit to the objective unit with an excess length that is at least half of, such as by being at least equal to, the outer circumference of the objective unit between the objective unit and the proximal unit, b) to adjust optimum optical image reproduction, the objective unit is rotated relative to the proximal unit about the longitudinal axis of the endoscope shaft, wherein c) the objective unit is fixed against rotation with the proximal unit after reaching an optimum position for optical image reproduction.

The endoscope can be installed with such method, where such method serves the same objectives as discussed above with regard to the endoscope.

In method step a), the excess length of the cable can be inserted into a peripheral groove that has a cross-sectional area that corresponds to a cross-sectional area that is at least three times, such as being more than five times, the cross-sectional area of the cable, as well as a height that at least corresponds to the thickness of the cable.

In method step a), the cable with its excess length can be wound around the circumference of the objective unit, and in method step c), the cable can be unwound out of its maximum wound position during the rotation of the objective unit. The wire, or respectively the cable is thereby wound around the objective unit before alignment. Depending on the desired alignment, this can be done at around half of the circumference of the objective unit for an alignment of ±180°, or at least once around the entire circumference for an alignment of 360°. The rotation is opposite the winding direction which unwinds the cable. If such a large rotational angle is needed that the cable is largely or completely unwound, it can also be placed in a loop around the objective unit.

In method step a), the cable with its excess length can be first inserted in the groove without being wound around the objective unit.

In the interest of the safety of the electrical feed-through, the rotation of the objective unit is limited before reaching a maximum deflection of the excess length of the cable.

In one embodiment, the objective unit can also be shifted in the longitudinal direction of the endoscope shaft relative to the proximal unit.

The objective unit can be introduced into a jacket tube together with the proximal unit and the cable before or after method step b).

Further features will become apparent from the description of embodiments together with the claims and the included drawings. Embodiments can fulfill individual characteristics or a combination of several characteristics.

BRIEF DESCRIPTION OF THE DRAWINGS

The embodiments are described below, without restricting the general idea, based on an exemplary embodiment in reference to the drawing, whereby we expressly refer to the drawing with regard to the disclosure of all details that are not explained in greater detail in the text.

The FIGURE schematically illustrates a cross-section of the distal region of an endoscope shaft 4 of an endoscope 2.

DETAILED DESCRIPTION

The endoscope shaft 4 is elongated along a longitudinal axis 6. In addition, beam paths 8, 8', 8" through the different lens groups of the endoscope 2 are also drawn. From the left, these pass through an entry window 22 into a first lens group with the lenses $24^I$, $24^{II}$, $24^{III}$, $24^{IV}$ and are guided by a second lens group with lenses $24^V$, $24^{VI}$, $24^{VII}$, $24^{VIII}$ further toward the image sensor 56 protected by the light passage windows $54^V$, $54^{II}$. The image sensor 56 is connected to control and deflection electronics 58 that control image recording and evaluation.

The lenses $24^I$ to $24^{VIII}$ form the lens groups of an objective unit 20 that are held in an objective tube 26 of the objective unit 20. Arranged around the objective tube 26 is an electromagnetic actuator 30 that has a coil 32, two permanent magnet rings 34, 35 and a yoke 36 on the outside of the objective tube 26, as well as a rotor 38 on the inside of the objective tube 26 that is magnetically operatively connected to the outer parts of the actuator 30 and can be shifted to two end positions by applying and not applying current to the coil 32. These end positions are defined by a distal stop 40 and a proximal stop 42 that are arranged on a holder 28 for the front-most lens group of the objective unit 20, or respectively on the objective tube 26 itself. An additional holder 29 holds the entry window 22.

A proximal section of the objective tube 26 in which also the lenses $24^{VI}$, $24^{VII}$, $24^{VII}$ are arranged is inserted into a proximal tube 52 of a proximal unit 50 and is rotatably mounted therein about the longitudinal axis 6. The proximal unit 50 comprises the light passage windows $54^I$, $54^{II}$, an image sensor 56 and a control and readout electronics 58.

Schematically portrayed between the proximal unit 50 and the objective unit 20 is an electrical feed-through 10, portrayed oversize, which comprises a cable 12 that has an excess length 14, and its excess length 14 is arranged in a groove 18, wherein the cable describes a winding 16 about the outer circumference of the objective unit 20, or respectively the groove 18. In this case, the excess length is 360° or more of the outer circumference of the objective unit 20. The cable 12 terminates in the coil 32 of the actuator 30. The groove 18 offers enough space for the cable 12 to unwind about the longitudinal axis 6 of the endoscope shaft 4 upon rotation of the objective unit 20 relative to the proximal unit 50. It is alternatively possible to align the objective unit 20 relative to the proximal unit 50 before insertion into a jacket tube, not shown in the FIGURE, and for the excess length 14 of the cable 12 to disappear into the groove 18, or respectively a suitable gap, before insertion into the jacket tube, or to align the objective unit 20 relative to the proximal unit 50 entirely within the jacket tube.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

- 2 Endoscope
- 4 Endoscope shaft
- 6 Longitudinal axis
- 8, 8', 8" Beam path
- 10 Electrical feed-through
- 12 Cable
- 14 Excess length
- 16 Winding
- 18 Groove
- 20 Objective unit
- 22 Entry window
- 24$^{I\text{-}VIII}$ Lenses
- 26 Objective tube
- 28, 29 Holder
- 30 Electromagnetic actuator
- 32 Coil
- 34 Permanent magnet ring
- 35 Permanent magnet ring
- 36 Yoke
- 38 Rotor
- 40 Distal stop
- 42 Proximal stop
- 50 Proximal unit
- 52 Proximal tube
- 54$^{I,II}$ Light passage window
- 56 Image sensor
- 58 Control and evaluation electronics

What is claimed is:

1. A method for assembling an endoscope having a distal electrical feed-through, the method comprising:

installing a cable at a transition from a proximal unit having a proximal optical assembly to a distal objective unit having a electromagnetic actuator and a distal optical assembly that can be shifted in a longitudinal direction by actuation of the actuator with an excess length between the distal objective unit and the proximal unit, the cable being fed from the proximal unit to the distal objective unit to supply current to the actuator, adjusting optimum optical image reproduction by rotating the distal objective unit relative to the proximal unit about the longitudinal axis of an endoscope shaft having the distal objective unit and the proximal unit, and fixing the distal objective unit against rotation with the proximal unit after the adjusting.

2. The method according to claim 1, wherein the installing comprises inserting the excess length of the cable into a peripheral groove having a cross-sectional area that is at least three times a cross-sectional area of the cable and a height that at least corresponds to a thickness of the cable.

3. The method according to claim 2, wherein the installing comprises inserting the cable with its excess length in the groove without being wound around the distal objective unit.

4. The method according to claim 1, wherein the installing comprises winding the cable with its excess length around a circumference of the distal objective unit, and the adjusting comprises unwinding the cable during the rotation of the distal objective unit.

5. The method according to claim 1, further comprising limiting rotation of the distal objective unit before reaching a maximum deflection of the excess length of the cable.

6. The method according to claim 1, further comprising shifting the distal objective unit in the longitudinal direction of the endoscope shaft relative to the proximal unit.

7. The method according to claim 1, prior to or subsequent to the adjusting, introducing the distal objective unit into a jacket tube together with the proximal unit and the cable.

\* \* \* \* \*